US005895811A

United States Patent [19]

Brust et al.

[11] Patent Number: 5,895,811
[45] Date of Patent: *Apr. 20, 1999

[54] ARTIFICIAL POSITIVE CONTROLS DERIVED FROM BIFUNCTIONAL CONJUGATES

[75] Inventors: Stefan Brust, Marburg-Michelbach; Heinz-Juergen Friesen, Marburg; Guenther Nau, Marburg-Schroeck; Hans-Erwin Pauly, Dautphetal, all of Germany

[73] Assignee: Behring Diagnostics GmbH, Marburg, Germany

[*] Notice: This patent is subject to a terminal disclaimer.

[21] Appl. No.: 08/469,003

[22] Filed: Jun. 5, 1995

Related U.S. Application Data

[62] Division of application No. 08/221,447, Apr. 1, 1994, Pat. No. 5,491,218, which is a continuation of application No. 07/958,713, Oct. 9, 1992, abandoned.

[30] Foreign Application Priority Data

Oct. 14, 1991 [DE] Germany ................ 4133945

[51] Int. Cl.$^6$ ............ C07K 16/46; C07K 16/42; G01W 33/531
[52] U.S. Cl. ............ 530/387.3; 530/388.3; 530/388.4; 530/388.5; 530/388.6; 530/389.4; 530/389.5; 530/861; 530/862; 530/863; 530/867; 530/391.1; 530/866; 530/402; 530/395; 530/396; 530/388.25; 424/136.1; 424/178.1; 435/972; 435/967; 436/547
[58] Field of Search ............ 530/387.3, 388.3, 530/388.4, 388.5, 388.6, 389.4, 389.5, 861, 862, 863, 867, 391.1, 866, 402, 395, 396, 388.25, 389.3; 424/136.1, 178.1; 435/972, 967, 7.1; 436/547

[56] References Cited

U.S. PATENT DOCUMENTS 5,635,600    6/1997    Fanger et al. .............. 530/387.3

FOREIGN PATENT DOCUMENTS

| 0 062 227 A1 | 3/1982  | European Pat. Off. . |
| 0 291 086 A3 | 5/1988  | European Pat. Off. . |
| 31 12 334 A1 | 10/1982 | Germany . |
| 38 00 048 A1 | 11/1988 | Germany . |

OTHER PUBLICATIONS

Nakamura et al., Chapter 27, vol. 1: 27.1–27.20. ImmunoChemistry from Handbook of Exp. Immunol. in four vols., ed. D. M. Weir, black Scientific Pub. (1984).

Annales de biologie clinque, R.G. Hamilton, vol. 48 (7): 473–477 (1990), Engineered Human Antibodies as Immunologic Quality Control Reagents.

Trends in Biotechnology, G. Williams, Feb. 1988, vol. 6, No. 2, Cambridge, Great Britain, Novel Antibody Reagents: Production and Potential.

*Primary Examiner*—Ronald B. Schwadron
*Attorney, Agent, or Firm*—Finnegan, Henderson, Farabow, Garrett & Dunner, L.L.P.

[57] ABSTRACT

The invention relates to an artificial positive control reagents based on antibody conjugates that are used in immunochemical detection methods and to processes for the preparation of these reagents.

8 Claims, 1 Drawing Sheet

ARTIFICIAL POSITIVE CONTROLS DERIVED FROM BIFUNCTIONAL CONJUGATES

This is a divisional application of Ser. No. 08/221,447, filed Apr. 1, 1994, now U.S. Pat. No. 5,491,218, which is a continuation of application Ser. No. 07/958,713, final Oct. 9, 1992, now abandoned.

BACKGROUND OF THE INVENTION

The invention relates to artificial standard and control reagents for use in immunochemical detection methods and to processes for the preparation of these reagents.

Customary immunological methods for diagnosing diseases associated with production of specific antibodies against any pathogen such as viruses, bacteria, allergens, autoantigens or certain pharmaceuticals are based on the ability of these antibodies to form complexes with antigenic structures on the causative agent. In some of these methods, a sample whose content of specific antibodies is to be tested is contacted with the antigenic structures of the pathogen, these antigenic structures being attached to suitable carrier materials. Specific antibodies which are present in the sample are bound and detected as immune complex with the antigenic structures of the pathogen which are immobilized on the carrier material. It is possible to use for this antibodies or other receptors, for example protein A, which are able to form complexes with the specific antibody in the sample. As a rule, the detection reagent carries a label which makes it possible to establish the amount of the bound specific antibody by measurement techniques. Commonly used labels are: radioactive isotopes, enzymes, fluorescent, phosphorescent or luminescent substances, substances with stable, unpaired electrons, erythrocytes, latex particles, metal sols.

Control and standard sera which contain a defined quantity of the antibodies to be detected are required for these immunochemical methods. A positive control serum of this type makes it possible to test the utilizability of the reagents used in the assay. Standardization and thus comparability of assay results which have been obtained on different days or in different laboratories additionally become possible. Quantitative determinations are possible with the aid of standard sera.

A technique which is frequently practiced for the preparation of positive control or standard sera comprises taking blood from patients whose disease is caused by defined causative agents, obtaining the serum, and adjusting the control or standard serum to a particular content of specific antibodies directed against the pathogen by mixing sera from different patients.

The disadvantages of this method are that a sufficient number of people whose blood contains these antibodies must be available. Furthermore, there are often medical reasons for not taking blood from such people, for example in the case of children, or there is a risk that the blood of the patient is infectious and no suitable methods for killing this pathogen are known.

DESCRIPTION OF THE RELATED ART

DE-A-31 12 334 describes artificial standard and control sera and processes for the preparation thereof and the use thereof, which do not have the abovementioned disadvantages. The standard and control reagent used is a chemically linked conjugate of two components A and B, where component A in the conjugate confers the ability to form complexes with the antigenic structures in the pathogen, and component B represents a human immunoglobulin or immunoglobulin fragment of that class which is to be measured in the immunochemical detection method. Thus, in order to prepare a conjugate as claimed in DE-A-31 12 334, it is necessary to isolate component B, i.e. human immunoglobulin of class G, M, A, D or E, in large quantity and in extremely high purity from human serum. An identical procedure for preparing artificial standard and control reagents is described in 1988 in DE-A-38 00 048.

The disadvantages of these processes are that an elaborate purification process is necessary to obtain the immunoglobulins, and this purification procedure leads to loss of or alteration in antigenic structures of the immunoglobulins. Thus, for example, human immunoglobulin M is prone to aggregate formation in all known purification processes, which impairs its utility for the preparation of conjugates of the type described above. In the case of other immunoglobulins, for example of the IgE class, the concentrations normally occurring in human sera are below 100 µg/l. To purify human IgE it is therefore necessary to have recourse to blood donated by myeloma IgE patients, of whom only a few are known world-wide, and whose blood samples are correspondingly rare and costly.

SUMMARY OF THE INVENTION

Control sera within the meaning of this invention also include standard sera.

The object therefore was to find artificial standard and control sera which do not have the disadvantages of the conjugates described above.

Surprisingly, it has been found that a suitable artificial standard and control serum can be obtained by preparing a conjugate of a component A which represents a binding factor for structural features of the pathogen, such as, for example, an antibody directed against this structural feature, and of a component B which is able to bind to specific structural features of the binding factor to be detected, which is directed against the pathogen, without restricting the immunochemical reactivity thereof. This conjugate is added in a suitable concentration to blood, blood components or sample fluid from healthy individuals. The resulting product is then employed for standard or control purposes.

It has emerged that conjugates of the components A and B just described can be prepared reproducibly, and a reagent with excellent suitability for checking function or for standardization can be obtained in conjunction with the natural content of immunoglobulins in the blood, in blood components or other sample fluids from non-patients.

The invention thus relates to standard and control sera for use in immunochemical detection methods for antibodies of particular antibody classes in body fluids from mammals, these antibodies being specifically directed against particular pathogens, characterized in that these standards and control sera contain conjugates of an analyte-specific and of an antibody-specific binding portion in the presence of the specific antibody class which is to be detected in the mammal, where the conjugate as such is not recognized as immunochemical equivalent to the antibody to be detected.

BRIEF DESCRIPTION OF THE DRAWING

FIG. 1. Comparison of prior art positive control with an artificial positive control. FIG. 1A shows a prior art immunoassay to detect antibodies that are specific for a particular pathogen and are of a specific immunoglobulin (Ig) class. Pathogen-specific antibodies of a particular Ig-class (the analyte), if present, bind to pathogen that is bound to a solid phase. The bound pathogen-specific antibodies are detected using a labeled antibody that is specific for the immunoglobulin class of the analyte. In the illustrated embodiment, the label is an enzyme (Enz) conjugated to the antibody. The positive control is a pathogen-specific antibody of the immunoglobulin class that is to be measured.

FIG. 1B shows an artificial positive control. A bifunctional conjugate binds specifically to the pathogen, and also binds to immunoglobulins of the class to be assayed. The immunoglobulins that bind to the bifunctional conjugate need not be specific for the pathogen. The artificial positive control bound to the solid phase is detected by a labelled antibody specific against the immunoglobulin class that is bound to the bi-functional conjugate.

FIG. 1C is similar to FIG. 1B, but shows that the bi-functional conjugate comprises two components. The component which binds to the pathogen (component A) is an antibody that is specific for the pathogen. Component A is linked to a second component (component B) which is an antibody directed against immunoglobulins of the immunoglobulin class be detected in the assay. The "artificial positive control" comprises the bi-functional conjugate and bound immunoglobulins of the class to be detected.

DESCRIPTION OF THE PREFERRED EMBODIMENTS

Figure 1A:
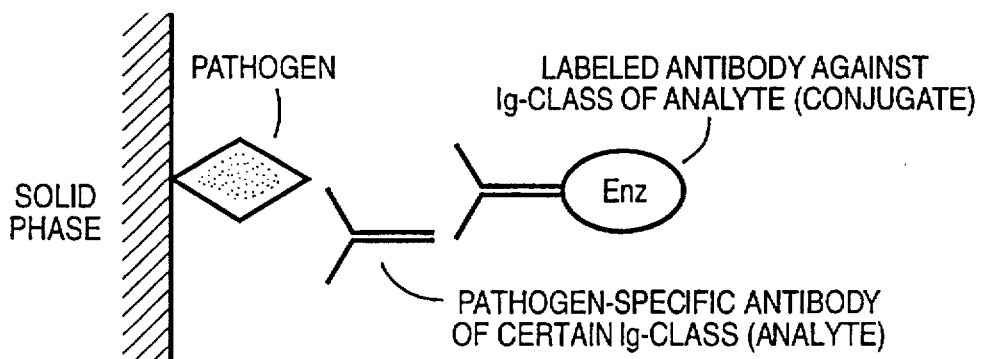
FIG. 1A depicts the prior art and FIGS. 1B and 1C depict embodiments of the claimed invention. The Figures are illustrative and are not intended to limit the present invention.
Figure 1B:
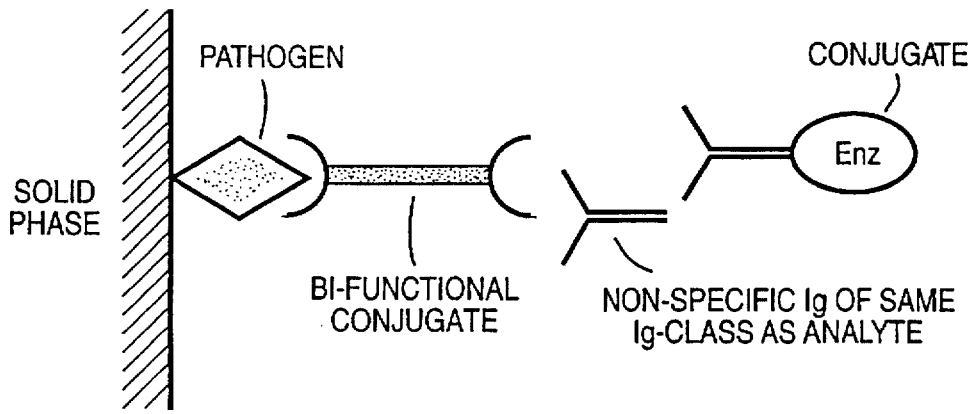
Figure 1C:
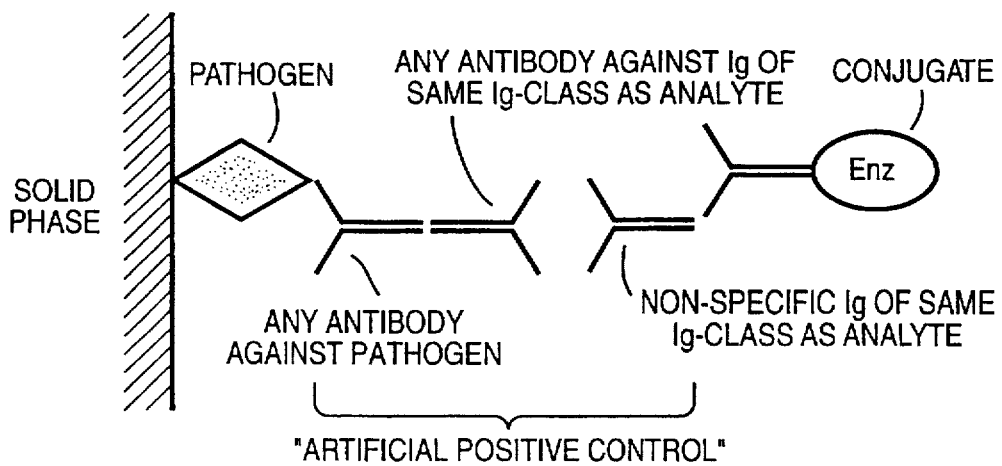

Preferred standard or control sera in this connection are those in which the antibodies to be detected are of human origin.

Further preferred standard or control sera are those in which the analyte-specific and antibody class-specific binding portions are monoclonal antibodies or antibody fragments.

Structural features of the pathogen are antigens, for example proteins, glycoproteins. It is possible and preferred for component A of the conjugate to be formed by polyclonal or monoclonal antibodies or fragments thereof, which can be prepared against structural features of the pathogen by processes known to the person skilled in the art, as well as lectins or other receptors. Component A is preferably of non-human origin.

Non-human within the meaning of this invention means that the molecule identified as such is not recognized as such by specific binding partners which are employed for detecting the analyte antibodies.

Monoclonal antibodies are particularly preferred.

Component B is preferably likewise composed of polyclonal or monoclonal antibodies, or fragments thereof, which are directed against the antibody to be detected, or of binding factors, for example lectins or protein A, which are able to react specifically with structural features of the antibody to be detected.

Antibodies are particularly preferred, and monoclonal antibodies are very particularly preferred. Component B is preferably also of non-human origin.

A conjugate within the meaning of the invention means any construct in which components A and B are linked while retaining their immunochemical function. Methods familiar to the person skilled in the art for preparing such conjugates are, for example, linkage by chemical reagents or by bioaffinity interaction. It is, however, also possible to produce hybrid molecules by chemical synthesis, the hybridoma technique or genetic engineering methods.

Antibodies within the meaning of this invention also include the antibody fragments which are relevant in each case and are known per se to the person skilled in the art.

A typical process for preparing the sera according to the invention appears is as follows:

Monoclonal antibodies against an analyte antigen are prepared by processes known to the person skilled in the art.

The analyte-specific antibodies are linked by the process described in Example 1 to monoclonal antibodies which are specifically directed against the antibody class to be detected.

The conjugate is purified, for example, by gel chromatography. It is advantageous for the conjugate subsequently to be concentrated, for example by dialysis, preferably to 1 to 10 mg/ml, and to be stabilized by methods known to the person skilled in the art. Defined amounts of this conjugate are added to a particular volume, for example of a normal human serum free of analyte antibodies. This standard or control serum obtained in this way can be stabilized and rendered storable in a way known to the person skilled in the art.

The serum is employed for use in the way known to the person skilled in the art.

The process according to the invention is characterized by its universal applicability. No restrictions which would impair application of the processes used in the examples to other conjugates are known.

The process according to the invention can also be applied to non-human control sera, it being essential that the conjugate which is employed is not recognized as such by the molecule employed as labeling receptor in the relevant assay method but is recognized only after binding to a molecule specific for the particular animal species and antibody class.

The standard and control sera according to the invention can be used in a large number of human and veterinary diagnostic methods. Examples to be mentioned are detection of antibodies of various immunoglobulin classes against structural features of viruses, for example viruses of hepatitis A, B, C, various HIV types, of rubella, cytomegaly, measles, mumps, varicella, herpes simplex and Epstein-Barr virus, of bacterial and parasitic pathogens, such as syphilis, borreliosis, toxoplasmosis, and of allergic disorders, for example the detection of allergy-specific IgE antibodies, of autoimmune diseases, and the detection of humoral defense reactions in patients who have possibly received administration of immunogenic agents for diagnostic or therapeutic purposes. Examples thereof are monoclonal antibodies against tumor-associated structures, and recombinant proteins with cytokine-like or coagulant properties.

The invention is illustrated by the following examples:

EXAMPLE 1

Preparation of a positive control serum for anti-HBcAg IgM 1 ml of 0.2M Li $BO_3$/20% dioxane is added to 4 mg of monoclonal anti-HBcAg antibody (in 1 ml of PBS pH 7.2), and a 15-fold molar excess of N-γ-maleimidobutyryloxysuccinimide (GMBS) is added, and the mixture is incubated at room temperature for 1 h. The unreacted heterobifunctional reagent is removed by gel chromatography (SEPHADEX G-25, a treated gel prepared by cross-linking dextran with epicholohydrin under alkaline conditions) with 0.1 molar sodium phosphate buffer +5 mM nitrilotriacetic acid (NTA) pH 6.0.

2 mg of monoclonal anti-human IgM antibodies (in 2 ml of 10 mM sodium phosphate, 100 mM NaCl, pH 7.4) are incubated with a 24-fold molar excess of N-succinimidyl 3-(2-pyridyldithio)propionate (SPDP) at room temperature for 30 minutes and then reduced with a 100-fold molar excess (compared with SPDP)of dithiothreitol (DTT) at RT for 15 minutes. After the reduction has taken place, the excess of reagents is removed by gel chromatography (SEPHADEX G-25) with 0.1M sodium phosphate/5 mM NTA pH 6.0.

The SH-activated anti-human IgM is incubated with the activated anti-HBcAg at RT for 2 hours and subsequently stopped with 1/10 the volume of 0.1M N-ethylmaleimide. The conjugate is purified by gel chromatography (ACA 34, LKB) with 50 mM Tris/HCl pH 7.4, and subsequently concentrated to 3 ml and stabilized with HSA. 50 µl, 25 µl, 12.5 µl and 6.25 µl of this conjugate (concentration=2 mg/ml) are pipetted into 1 ml of normal human serum (anti-HBc IgM negative), filtered through 0.2 µm Sartorius membrane filters and stored at +2 to +8° C.

EXAMPLE 2

Use of the conjugates in an enzyme immunoassay

In an enzyme immunoassay to detect IgM antibodies against HBcAg (ENZYGNOST, an ELISA-type immunoassay (enzyme-linked immunosorbent assay) anti-HBcAg/ IgM assay kit of Behringwerke AG, Marburg, FRG), 10 µl of a serum which has previously been diluted 1:100, or of the artifical positive control prepared as in Example 1, and 90 µl of sample buffer are incubated in microtiter plates coated with anti-human IgM at 37° C. for one hour, washed in accordance with the package insert, incubated with 100 µl of HBcAg-POD conjugate at 37° C. for one hour, washed again, incubated with 100 µl of tetramethylbenzidine (TMB) substrate solution in accordance with the package insert at room temperature for 30 min, stopped with 100 µl of 0.5M $H_2SO_4$ solution, and measured in a photometer at 450 nm.

The peroxidase marker enzyme catalyzes the conversion of the chromogen TMB into the dye; the color produced after 30 minutes is proportional to the content of antibodies directed against HBcAg in the sample. The extinctions obtained for the artificial positive control in the serial dilutions described in Example 1 are compared with the extinction for the negative control in Table 1:

TABLE 1

| Dilution of the artificial pos. control | Extinctions at 450 nm | Extinctions of the neg. control at 450 nm |
| --- | --- | --- |
| 1:20 | >3.000 | 0.056 |
| 1:40 | 2.583 | |
| 1:80 | 1.385 | |
| 1:160 | 0.638 | |

EXAMPLE 3

Preparation of a conjugate of anti-human IgM and of an anti-Herpes simplex virus (HSV) F(ab') fragment 10 mg of monoclonal antibodies against HSV (in 2 ml of 50 mM sodium acetate buffer pH 4.3) are incubated with 1 mg of pepsin at 37° C. for 24 h, and the reaction mixture is adjusted to pH 7.2 with about 0.2 ml of 2N NaOH. The F(ab')$_2$ fragment is purified by gel chromatography (ACA-44 supplied by LKB) with 50 mM Tris/HCl pH 7.4, and subsequently concentrated to 1 ml (about 5 mg of F(ab')$_2$ fragment) and reduced to F(ab') with 0.1 ml of 0.1M cysteamine HCl solution at RT for 60 minutes and subsequently chromatographed on SEPHADEX G-25 (column 1 cm vol. 10 ml). The reduced anti-HSV F(ab') fragment is reacted with 5 mg of activated anti-human IgM-maleimide (see above) at 37° C. for 1 hour. Unreacted antibody F(ab') fragment is separated from the actual conjugate by gel chromatography (ACA-34 LKB) with 50 mM Tris/HCl pH 7.4, subsequently concentrated to 5 ml and stabilized with HSA.

EXAMPLE 4

Anti-GM-CSF IgM positive control sera

An F(ab') fragment of a rabbit anti-GM-CSF antibody was conjugated to a mouse anti-human IgM antibody in analogy to Example 3.

We claim:

1. A bi-functional conjugate comprising an antibody of non-human origin, wherein said conjugate has a) a first binding site that specifically binds the specific pathogen; and b) a second binding site that specifically binds a specific class of immunoglobulin;

wherein the first binding site is an antibody fragment, or the second binding site is an antibody fragment, or both the first binding site and the second binding site are antibody fragments.

2. The conjugate of claim 1 comprising an F(ab') antibody fragment.

3. The conjugate of claim 1 wherein both the first and the second binding sites are antibody fragments.

4. The conjugate of claim 1 wherein the first binding site is an antibody fragment and the second binding site is not an antibody fragment.

5. The conjugate of claim 1 wherein the second binding site is an antibody fragment and the first binding site is not an antibody fragment.

6. An artificial positive control comprising the conjugate of claim 1, wherein said second binding site of said conjugate is bound to an antibody of said specific class of immunoglobulin.

7. The artificial positive control comprising the conjugate of claim 1 in a human serum.

8. The conjugate of claim 1 wherein at least one antibody fragment comprising said conjugate is a fragment from a monoclonal antibody.

* * * * *

UNITED STATES PATENT AND TRADEMARK OFFICE
CERTIFICATE OF CORRECTION

PATENT NO. : 5,895,811
DATED : April 20, 1999
INVENTOR(S) : BRUST et al.

It is certified that error appears in the above-identified patent and that said Letters Patent is hereby corrected as shown below:

On the Title Page, Item [57], in the Abstract, line 1, before "artificial", delete "an".

Signed and Sealed this

Thirtieth Day of November, 1999

Attest:

Q. TODD DICKINSON

*Attesting Officer*     *Acting Commissioner of Patents and Trademarks*